(12) United States Patent
Billet et al.

(10) Patent No.: US 6,244,869 B1
(45) Date of Patent: Jun. 12, 2001

(54) FRAME MADE OF COMPOSITE MATERIAL FOR A REMOVABLE DENTAL PROSTHESIS, AND MANUFACTURING PROCESS

(76) Inventors: Gilles Billet, 32 Avenue D'Haussez, F-38500 Voiron; Bruno Clunet Coste, Tolvon, F-38960 Saint Etienne de Crossey; Andre Collombin, 22 Rue du Lavoir de Criel; Bernard Maneuf, Hameau de Vouise, both of F-38500 Voiron, all of (FR)

( * ) Notice: Subject to any disclaimer, the term of this patent is extended or adjusted under 35 U.S.C. 154(b) by 0 days.

(21) Appl. No.: 09/424,448
(22) PCT Filed: Mar. 23, 1999
(86) PCT No.: PCT/FR99/00677
    § 371 Date: Nov. 23, 1999
    § 102(e) Date: Nov. 23, 1999
(87) PCT Pub. No.: WO99/48434
    PCT Pub. Date: Sep. 30, 1999

(30) Foreign Application Priority Data
Mar. 25, 1998 (FR) .................................................. 98 03931

(51) Int. Cl.⁷ .................................................. A61C 13/00
(52) U.S. Cl. ............................................................ 433/199.1
(58) Field of Search ................................... 433/213, 171, 433/199.1

(56) References Cited

U.S. PATENT DOCUMENTS

| 2,418,833 | 4/1947 | Harris et al. |
| 4,654,006 | * 3/1987 | Kusano et al. .................... 433/199.1 |
| 4,816,194 | * 3/1989 | Katayama et al. .................. 433/213 |
| 4,894,012 | 1/1990 | Goldberg et al. |
| 5,676,546 | 10/1997 | Heitmann et al. |

FOREIGN PATENT DOCUMENTS

| WO 90/11732 | 10/1990 | (WO) . |
| WO 95/08300 | 3/1995 | (WO) . |
| WO 96/15731 | 5/1996 | (WO) . |
| WO 96/25911 | 8/1996 | (WO) . |
| WO 98/19621 | 5/1998 | (WO) . |

* cited by examiner

Primary Examiner—Todd E. Manahan
(74) Attorney, Agent, or Firm—Oliff & Berridge PLC

(57) ABSTRACT

A frame for a removable dental prosthesis has a base part having a layer of woven fabrics of a composite material, which is arranged as a support shell in the form of an arch designed to cover at least a part of the patient's jaw. An intermediate part extends along the top of the base part to form a beam having a good crushing strength, and forming the limits of the section of the frame. A surface part forms a cap totally covering the base part and intermediate part, the material of the cap being formed by a laminated fiber reinforcement material having an organic matrix of the same nature as that of the base part. The assembly, made up of the base part, the intermediate part and the surface part form, after shaping and polymerization, a self-supporting profiled part having a good breaking resistance.

12 Claims, 4 Drawing Sheets

FRAME MADE OF COMPOSITE MATERIAL FOR A REMOVABLE DENTAL PROSTHESIS, AND MANUFACTURING PROCESS

BACKGROUND OF THE INVENTION

The invention relates to a frame for a removable dental prosthesis made of a composite material with laminated fiber reinforcement, pre-impregnated with a resin in the state prior to polymerization.

STATE OF THE TECHNIQUE

Known frames generally comprise metal plates obtained by long and costly casting processes. The presence of such a rigid metal plate inside the mouth is both unaesthetic and uncomfortable.

It has already been proposed to replace the metal plates of removable dental prostheses by lighter plates made of acrylic resin, in which reinforcing fibres are coated (document U.S. Pat. No. 4,894,012). Incorporating a network or a bundle of fibres is however not sufficient to obtain a significant mechanical strength of the acrylic resin plates. The fibres constitute a simple internal net enabling the fractured parts not to be completely detached after the plate has broken in the mouth.

OBJECT OF THE INVENTION

A first object of the invention is to achieve a frame for a removable dental prosthesis, which is particularly lightweight and has a high mechanical strength.

A second object of the invention also aims to propose a manufacturing process of a removable dental prosthesis frame which is particularly simple and quick to implement.

The frame according to the invention is composed:
of a base part comprising a layer of woven fabric of said composite material, which is arranged as a support shell in the form of an arch,
of an intermediate part extending along the top of the base part to form a beam having a good crushing strength, and forming the limits of the profile of the frame,
and of a surface part forming a cap totally covering the base part and intermediate part, the material of the cap being formed by a laminated fiber reinforcement material having an organic matrix of the same nature as that of the base part, the assembly made up of the three parts forming after shaping and polymerization a self-supporting profiled part exhibiting a good resistance to fracture.

According to a preferred embodiment, the intermediate part is formed by a bundle of long and continuous fibres extending along the profile of the beam and housed in a sheath acting as a cover. The sheath is formed by a woven assembly of fibres, which can be of the same nature as the fibres of the material of the other two base and surface parts.

According to one feature of the invention, the intermediate part is equipped with a shaping device designed to surround and clamp the sheath and bundle of fibres to define a predetermined transverse cross section.

According to another feature of the invention, the base of the sheath presents a conjugate shape to that of the top of the base part, and has a higher mechanical strength than that of the rest of the woven assembly of fibres of said sheath.

A first manufacturing process of the frame according to the invention is characterized by the following stages:
in a first stage the base part is placed on a laboratory model, said part comprising a laminated fiber reinforcement material pre-impregnated with resin reinforced with fibres and particles,
the base part is shaped under isostatic pressure by compression following placing of said laminated fiber reinforcement material on the laboratory model,
the resin of the shaped base part is polymerized to obtain a support shell in the form of an arch,
in a second stage the intermediate part is placed on the top of the arch of the base part,
and in a third stage said intermediate part is covered by the surface part shaped under isostatic pressure to form said cap after polymerization.

A second manufacturing process is characterized in that:
the intermediate part is first applied along the top edge of a laboratory model, without crushing the fibres of the sheath,
pre-polymerization of the intermediate part is performed to determine the profile of the frame,
the intermediate part is removed and the base part is placed on the model without prior shaping and without polymerization,
the pre-polymerized intermediate part is placed on the base part again, and is covered with the surface part,
the assembly is then shaped under isostatic pressure, followed by the complete polymerization stage of the frame.

According to another feature of the process, reservation elements passing transversely through the base part, the intermediate part, and the surface part are incorporated in the self-supporting profiled part before the shaping and polymerization phase, each reservation element being made of a material incompatible with the composite material of the profiled part to insure easy extraction thereof after shaping. Retaining parts are inserted in the confined cavities after the reservation elements have been extracted, each retaining part being formed by a tab having a protruding part for receipt of an artificial tooth.

Such a frame for a removable dental prosthesis can be securely fixed to an attachment covering a root. The attachment comprises for this purpose
a male element formed by a cup filled with a photo curable composite material and fixed onto a root dental post or on a coronary reconstitution, said cup being made of a material transparent to electromagnetic rays and incompatible with the resin of the parts constituting the profiled part,
a female part composed of an envelope made of flexible material cooperating by engagement with the external face of the cup and secured to the self-supporting profiled part of the frame when the shaping operation is performed.

BRIEF DESCRIPTION OF THE DRAWINGS

Other advantages and features will become more clearly apparent from the following description of an illustrative embodiment of the invention, given as a non-restrictive example only and represented in the accompanying drawings, in which.

DETAILED DESCRIPTION OF PREFERRED EMBODIMENTS

Figure 1:
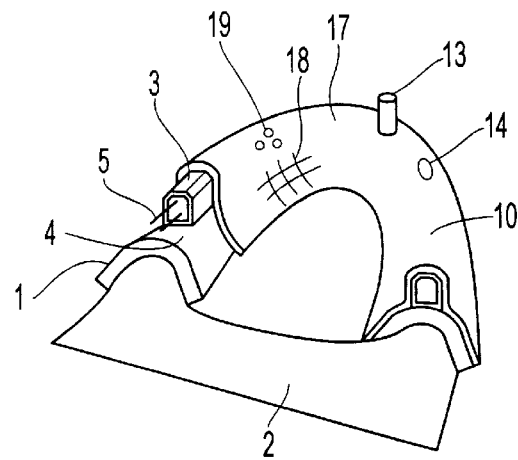
FIG. 1 is a perspective view of an frame for a removable dental prosthesis according to the invention.
Figure 2:
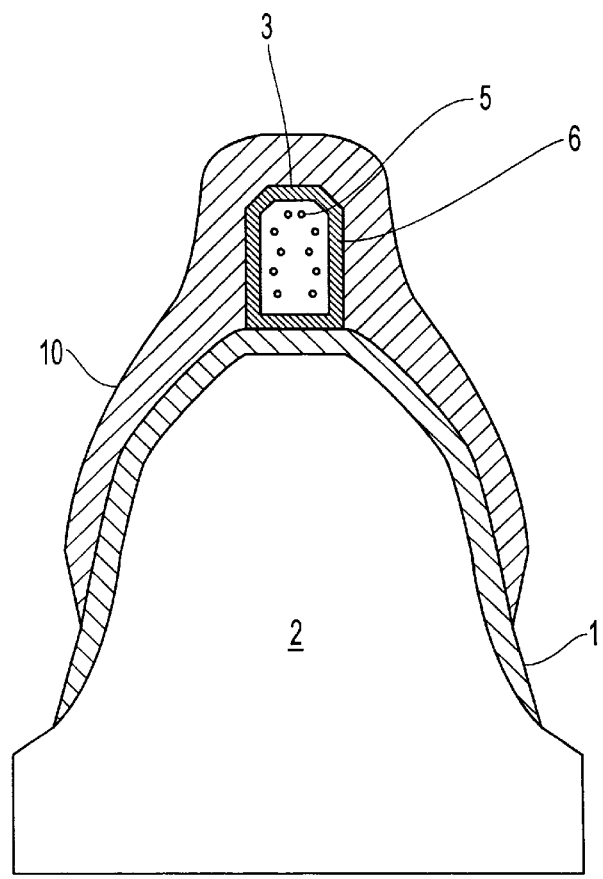
FIG. 2 represents a vertical cross sectional view of the self-supporting profiled part of the frame placed on a laboratory model.

With reference to FIGS. 1 to 4, an frame 12 for a removable partial or complete dental prosthesis is achieved by means of a composite resin material 17 with reinforcing fibres 18 and particles 19 constituting after shaping a rigid self-supporting profiled part 12 resistant to breaking. The reinforcing fibres 18 and particles 19 are arranged as a laminated fiber reinforcement assembly composed of one or more layers of woven fabric. The fibres can be glass, ceramic, aramide or silica fibres, pre-impregnated with a resin in the state prior to polymerization.

A first manufacturing process of a self-supporting profiled part 12 according to the invention is performed in three main stages:

in the course of a first stage, a base part 1 formed by a laminated fiber reinforcement material with pre-impregnated tissue is formed under isostatic pressure on a laboratory model 2 representative of the soft tissues. The laminated fiber reinforcement material shaping operation is performed by compression following placing of the base part 1 on the laboratory model 2 according to the process and the machine described in the document WO95/08300. The resin 17 of the base part 1 is for example a methacrylate or dimethacrylate resin, but any other type of organic resin suitable for dental use can be used, as mentioned in the above-mentioned document. The resin 17 with fiber 18 and particle 19 reinforcements moreover contains initiators agents and accelerating agents enabling cross-linking by photo curing. After the forming and photo-polymerization operations, the base part 1 is arranged as a support shell in the form of an arch following the outline of the laboratory model 2 exactly.

In a second stage, an intermediate part 3 is applied on the top 4 to form a beam presenting a high crushing strength. The intermediate part 3 is formed by a bundle of long and continuous fibres 5, which are housed in a sheath 6 formed by a woven assembly of fibres 8. The sheath 6 acts as a cover housing the pre-impregnated fibers 5 and comprises a base 7 of conjugate shape to that of the top 4 of the base part 1.

Figure 3:
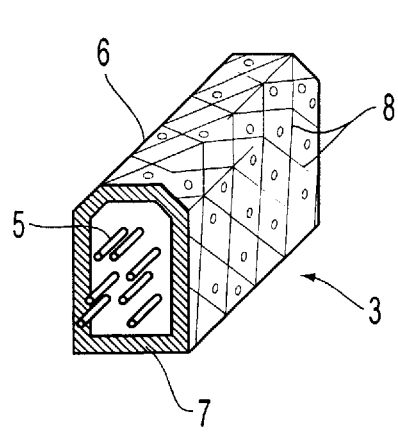
FIG. 3 is a partial view of the intermediate part of the frame.
Figure 4:
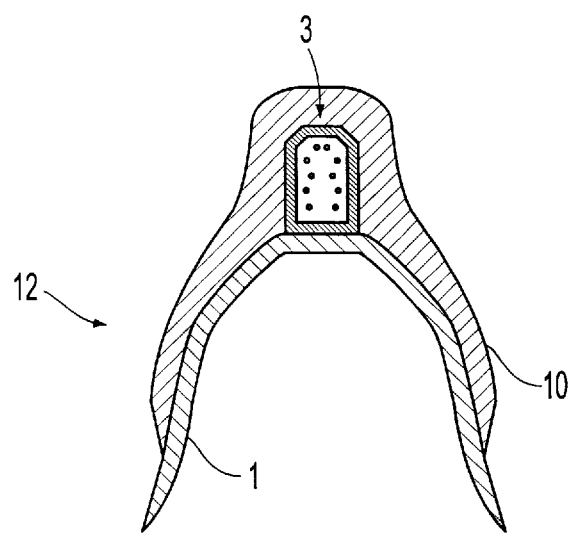
FIG. 4 is a reduced scale view of the profiled part of FIG. 2 after the laboratory model has been removed.

In FIG. 3, the base 7 of the sheath 6 is flat to obtain a good adherence surface with the top 4 of the base part 1. The rigidity of the base 7 is preferably greater than that of the rest of the woven assembly of the fibres 8 of the sheath 6.

The base 7 of the sheath 6 can advantageously be formed by a part of the base part 1.

In a third stage, a surface part 10 formed by a laminated material with a fabric of pre-impregnated fibres 18 and particles 19, of the same nature as that of the base part 1, is placed on the intermediate part 3, and is then shaped under isostatic pressure and photo-polymerized in the previously used shaping machine. The surface part 10 forms a cap totally covering the base part 1 and the intermediate part 3 so as to obtain a rigid self-supporting profiled part 12 exhibiting a good resistance to fracture.

The beam forming the intermediate part 3 is sandwiched between the two parts 1 and 10 to determine the section of the structure and the crushing strength. The base part 1 and surface part 10 ensure the mechanical rigidity of the structure after polymerization.

A second manufacturing mode of the self-supporting profiled part 12 can be implemented as follows:

The intermediate part 3 is first applied on the top of the laboratory model 2 without crushing the fibres 5 of the part 3 exposing it for a short time to light, so as to determine the section of the frame 12. After the intermediate part 3 has been removed, the base part 1 is placed on the laboratory model 2 without prior shaping and without polymerization. The pre-polymerized intermediate part 3 is placed on the base part 1 again and is covered with the surface part 10. The whole of the structure is then shaped under isostatic pressure in the shaping machine, followed by photo-polymerization.

Figure 5:
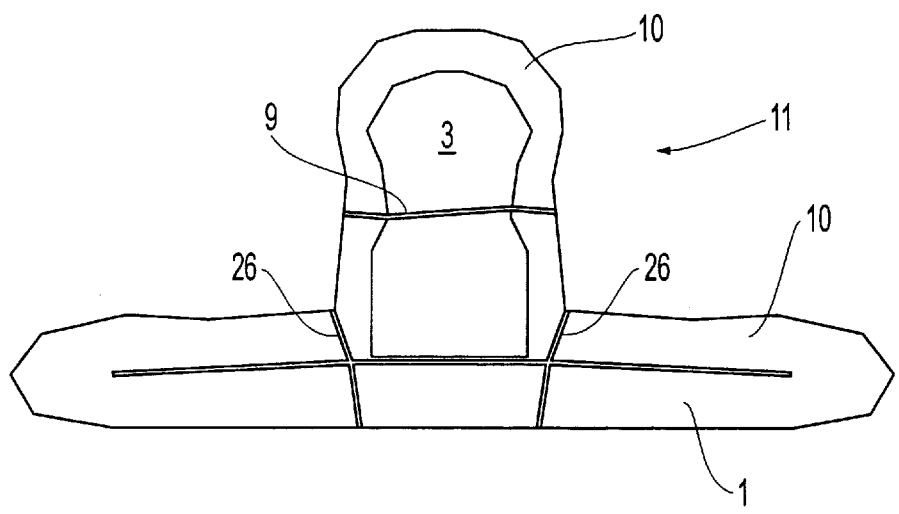
FIG. 5 shows a cross sectional view of an alternative embodiment of the self-supporting profiled part of the frame.

According to FIG. 5, it is possible to make use of a complex profiled part 11 in which the intermediate part 3 is not polymerized, and is equipped with a shaping device 9 designed to strangle the bundle of fibres 5 transversely to define a predetermined transverse cross section, for example Omega-shaped. The intermediate part 3 is sewn or soldered to the interfaces 26 between the base part 1 and the surface part 10. The edges of the join 12 of the base part 1 and the surface part 10 can also be sewn or soldered. Such a self-supporting profiled part 11 can be formed in a single manufacturing stage.

Figure 6:
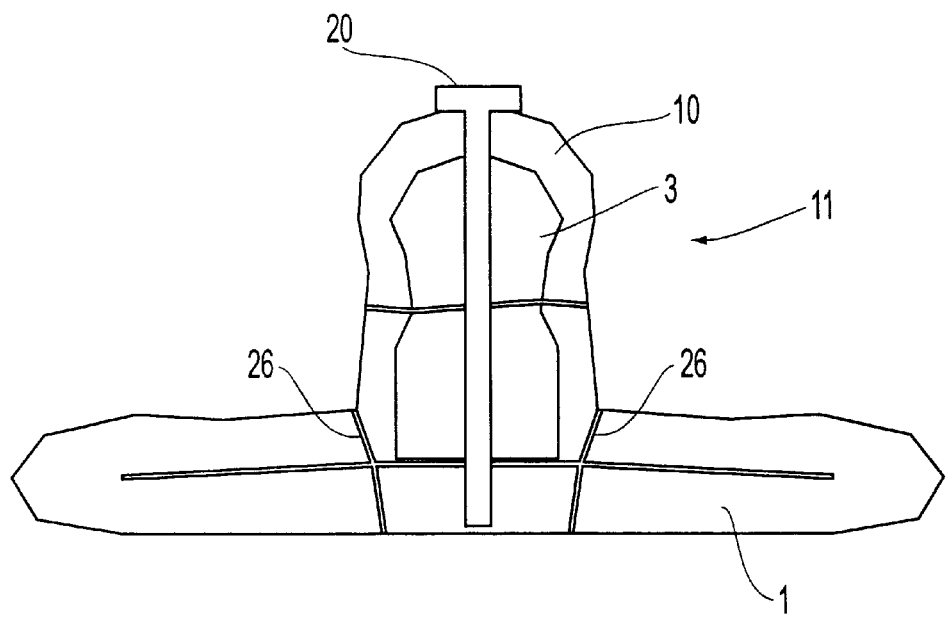
FIGS. 6 and 7 represent the complex profiled part of FIG. 5, respectively after fitting of reservation elements and retaining parts.
Figure 7:
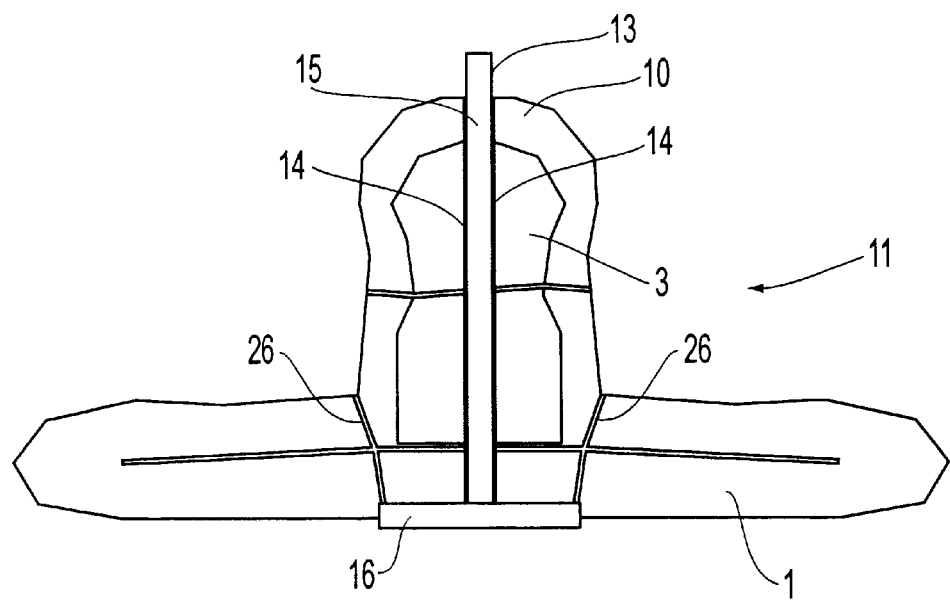

With reference to FIGS. 6 and 7, reservation elements 20 passing through the base part 1, the intermediate part 3, and the surface part 10 in a vertical direction are incorporated in the complex profiled part 11 before the shaping and polymerization phase. The reservation elements 20 are made from a material incompatible with the resin used for the profiled part 11, so as to prevent any adherence when shaping takes place. Subsequent extraction of the reservation elements 20 then forms the limits of cavities 14 for insertion of retaining parts 13 (FIG. 7). The retaining parts 13 are arranged as tabs 15 each provided with a protruding part for receipt of an artificial tooth, and a base part 16 in the form of an annular disk at the opposite end. Each retaining part 13 is made of a composite material of resin base 17 reinforced with fibres 18 and particles 19 of the same type as the self-supporting profiled part 12.

In a final manufacturing stage, the self-supporting profiled parts 12 are coated with an organic resin-based external finishing coating.

The advantage of these self-supporting structures for manufacture of dental prostheses lies in their lightness and their great flexibility in conjunction with a high mechanical strength providing a high degree of comfort in the patient's mouth. The absence of any metallic material enables them to be associated by suitable non-metallic attachments to the roots, if any.

Figure 8:
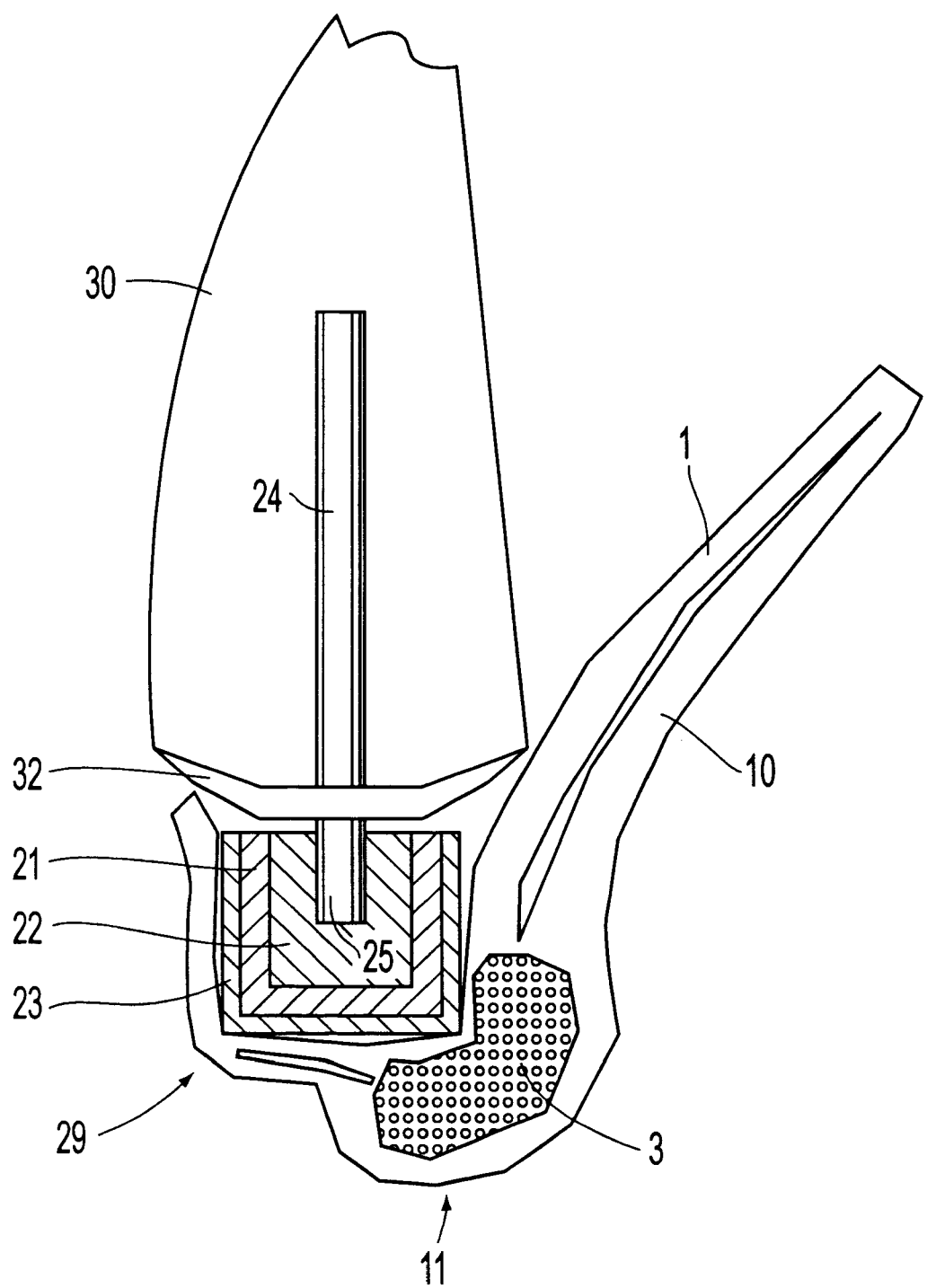
FIG. 8 shows an attachment of an frame according to the invention to a residual root of a tooth.

On the attachment 29 of FIG. 8, the root 30 of a tooth is capped by a plate 32 mounted on a post 24 having a protruding end 25. Such a coronary reconstitution is described in detail in the documents WO 95/08300 and WO 96/15731. A cup 21 made of ceramic material or glass is filled with photo curable composite material 22 and is fixed onto the end 25 of the post 24. The cup 21 constitutes the male attachment element 29 and can be made of any other material transparent to electromagnetic rays and incompatible with the resin of the parts constituting the profiled part 11, 12. The cylindrical cup 21 is coated with an envelope 23 made of flexible material, able to slide on the bearing surface of the cup 21 with a retaining effect. The envelope 23 constitutes the female attachment element 29. The state of the surface of the envelope 23 enables it to be secured with the self-supporting profiled part 11 when the shaping operation of the latter is performed, in particular when the base part 1 is applied on the model in the previously described second manufacturing process, before shaping and hardening.

What is claimed is:

1. An reinforcing frame for removable dental prosthesis made of a composite material with laminated fiber reinforcement of fibres (18), pre-impregnated with a resin (17) in the state prior to polymerization, characterized in that the frame (12) is composed:

of a base part (1) comprising a layer of woven fabric of said composite material, which is arranged as a support shell in the form of an arch, of an intermediate part (3) extending along the top (4) of the base part (1) to form a beam having a good crushing strength, and forming limits of the section of the frame (12), and of a surface part (10) forming a cap totally covering the base part (1) and intermediate part (3), the material of the cap being formed by a laminated fiber reinforcement material having an organic matrix of the same nature as that of the base part (1), the assembly made up of the three parts (1, 3, 10) forming after shaping and polymerization a self-supporting profiled exhibiting a good resistance to fracture.

2. The frame for a removable dental prosthesis according to claim 1, characterized in that the intermediate part (3) is formed by a bundle of long and continuous fibres (5) extending along the profile of the beam and housed in a sheath (6) acting as a cover.

3. The frame for a removable dental prosthesis according to claim 2, characterized in that the sheath (6) is formed by a woven assembly of fibres (8), which are of the same nature as the fibres (18) of the material of the other two base (1) and surface (10) parts.

4. The frame for a removable dental prosthesis according to claim 2, characterized in that the intermediate part (3) is equipped with a shaping device (9) designed to surround and clamp the sheath (6) and bundle of fibres (5) to define a predetermined transverse cross section.

5. The frame for a removable dental prosthesis according to claim 4, characterized in that the transverse cross section of the intermediate part (3) is Omega-shaped.

6. The frame for a removable dental prosthesis according to claim 2, characterized in that the base (7) of the sheath (6) presents a conjugate shape to that of the top (4) of the base part (1), and has a higher mechanical strength than that of the rest of the woven assembly of fibres (8) of said sheath (6).

7. The frame for a removable dental prosthesis according to claim 2, characterized in that the base (7) of the sheath (6) is formed by a part of the base part (1).

8. A manufacturing process of an frame for a removable dental prosthesis according to claim 1, characterized in that:

in a first stage the base part (1) is placed on a laboratory model (2), said part comprising a laminated fiber reinforcement material pre-impregnated with resin (17) reinforced with fibres (18) and particles (19), the base part (1) is shaped under isostatic pressure by compression following placing of said laminated fiber reinforcement material on the laboratory model (2), the resin (17) of the shaped base part (1) is polymerized to obtain a support shell in the form of an arch, in a second stage the intermediate part (3) is placed on the top of the arch of the base part (1), and in a third stage the intermediate part (3) is covered by the surface part (10) shaped under isostatic pressure to form said cap after polymerization.

9. The manufacturing process of an frame for a removable dental prosthesis according to claim 8, characterized in that reservation elements (20) passing transversely through the base part (1), the intermediate part (3), and the surface part (10) are incorporated in a self-supporting profiled part (11) before the shaping and polymerization phase, each reservation element (20) being made of a material incompatible with the composite material of the profiled part (11) insuring easy extraction thereof after shaping.

10. The manufacturing process of an frame for a removable dental prosthesis according to claim 9, characterized in that retaining parts (13) are inserted in confined cavities (14) after the reservation elements (20) have been extracted, each retaining part (13) being formed by a tab (15) having a protruding part for receipt of an artificial tooth.

11. A manufacturing process of an frame for a removable dental prosthesis according to claim 1, characterized in that:

the intermediate part (3) is first applied along the top edge of a laboratory model (2) without crushing the fibres (5) of the sheath (6), pre-polymerization of the intermediate part (3) is performed to determine the section of the frame, the intermediate part (3) is removed and the base part (1) is placed on the model (2) without prior shaping and without polymerization, the pre-polymerized intermediate part (3) is placed on the base part (1) again, and is covered with the surface part (10), the assembly is then shaped under isostatic pressure, followed by the complete polymerization stage of the frame.

12. An attachment device usable with a frame for a removable dental prosthesis, characterized in that the frame is removable, the attachment device comprising:

a male element formed by a cup (21) filled with a photo curable composite resin (22) and fixed onto the end (25) of a tab (24) of a root (30) or of a coronary reconstitution, said cup being made of a material transparent to electromagnetic rays and incompatible with the resin of the parts constituting the profiled part (11), a female part composed of an envelope (23) made of flexible material cooperating by engagement with the external face of the cup (21) and secured to the self-supporting profiled part (11) of the frame when the shaping operation is performed; and the frame, made of composite material with laminated fiber reinforcement of fibers (18) pre-impregnated with a resin (17) in the state prior to ploymerization, comprising:

a base part (1) having a layer of woven fabric of said composite material, which is arranged as a support shell in the form of an arch;

an intermediate part (3) extending along the top (4) of the base part (1) to form a beam having a good crushing strength and forming limits of the section of the frame (12); and a surface part (10) forming a cap totally covering the base part (1) and intermediate part (3), the material of the cap being formed by a laminated fiber reinforcement material having an organic matrix of the same nature as that of the base part (1), the assembly made up of the three parts (1, 3, 10) forming, after shaping and polymerizaton, a self-supporting profiled part exhibiting a good resistance to fracture.

* * * * *